US00PP21220P2

(12) United States Plant Patent
Topping

(10) Patent No.: US PP21,220 P2
(45) Date of Patent: Aug. 17, 2010

(54) ***CORDYLINE* PLANT NAMED 'NORFIRE'**

(50) Latin Name: *Cordyline australis*
Varietal Denomination: Norfire

(76) Inventor: Peter Topping, Northern Liners Co Ltd., Lancaster Road, Out Rawcliffe, Preston PR3 6SR (GB)

( * ) Notice: Subject to any disclaimer, the term of this patent is extended or adjusted under 35 U.S.C. 154(b) by 0 days.

(21) Appl. No.: 12/454,884

(22) Filed: May 26, 2009

(51) Int. Cl.
*A01H 5/00* (2006.01)

(52) U.S. Cl. ..... Plt./383

(58) Field of Classification Search ..... Plt./383
See application file for complete search history.

(56) References Cited

OTHER PUBLICATIONS

UPOV-ROM GTITM, Plant Variety Database, 2009/06, GTI Jouve Retrieval Software, citation for 'Norfire'.*

* cited by examiner

*Primary Examiner*—Susan B McCormick Ewoldt
(74) *Attorney, Agent, or Firm*—Penny J. Aguirre

(57) ABSTRACT

A new cultivar of *Cordyline australis,* 'NORFIRE', characterized by its plant habit that is dense and rounded and its numerous leaves that are short in length, narrow in width, and brown-purple in color.

2 Drawing Sheets

Botanical classification: *Cordyline australis.*
Cultivar designation: 'NORFIRE'.

BACKGROUND OF THE INVENTION

The present invention relates to a new and distinct cultivar of *Cordyline australis* and will be referred to hereafter by its cultivar name, 'NORFIRE'. 'NORFIRE' represents a new cultivar of cabbage tree or cabbage palm and is grown as a foliage plant for landscape and container use.

The Inventor discovered the new cultivar as a single plant in a block of young plants derived from tissue culture of *Cordyline australis* 'Red Star' (not patented) in Preston, Lancashire, United Kingdom in April of 2003.

Asexual reproduction of the new cultivar was first accomplished by in vitro propagation in September of 2004 in Preston, Lancashire, United Kingdom under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'NORFIRE' as a new and unique cultivar of *Cordyline.*

1. 'NORFIRE' exhibits foliage that is brown-purple in color.
2. 'NORFIRE' exhibits a greater number of leaves in comparison to its parent plant.
3. 'NORFIRE' exhibits leaves that are shorter in length and narrower in width in comparison to its parent plant and other cultivars known to the Inventor.
4. 'NORFIRE' exhibits a plant habit that is dense and rounded.

In comparison to the parent plant, 'Red Star', 'NORFIRE' differs in having foliage that is narrower in width, shorter in length, and brown-purple rather than red-brown in color and in having a denser more rounded plant habit with a greater number of leaves. 'NORFIRE' can also be compared to the cultivars 'Maroon Magic' (U.S. Plant Pat. No. 16,954) and 'Jel01' (U.S. Plant Pat. No. 18,545). Both 'Maroon Magic' and 'Jel01' have similar dark brown-purple to burgundy foliage, however they both differ most significantly in comparison to 'NORFIRE' in having leaves that are much wider and in having a more upright plant habits.

BRIEF DESCRIPTION OF THE DRAWING

The accompanying colored photographs illustrate the overall appearance and distinct characteristics of the new *Cordyline*. The photographs were taken in March of 3 year-old plants of 'NORFIRE' as grown in a 25-cm container under poly cover in Preston, Lancashire, United Kingdom.

DETAILED BOTANICAL DESCRIPTION OF THE PLANT

Figure 1:
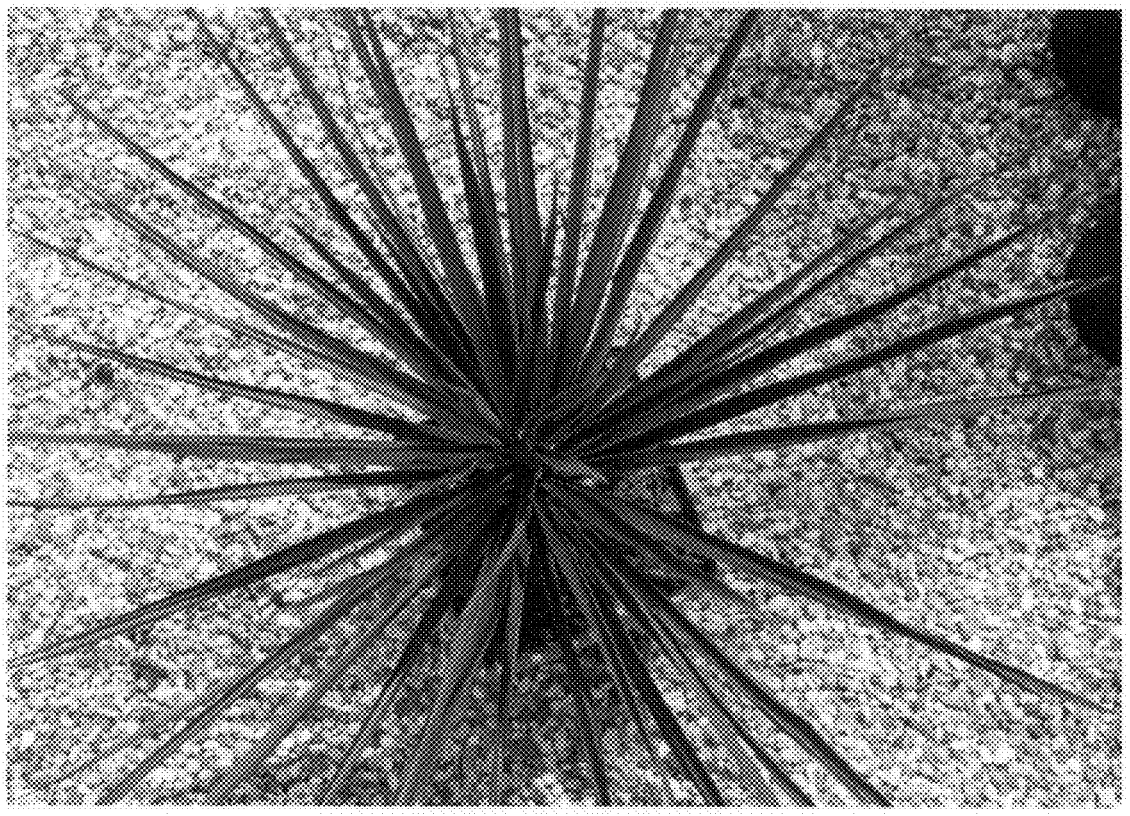
FIG. 1 provides a top view of 'NORFIRE'.
Figure 2:
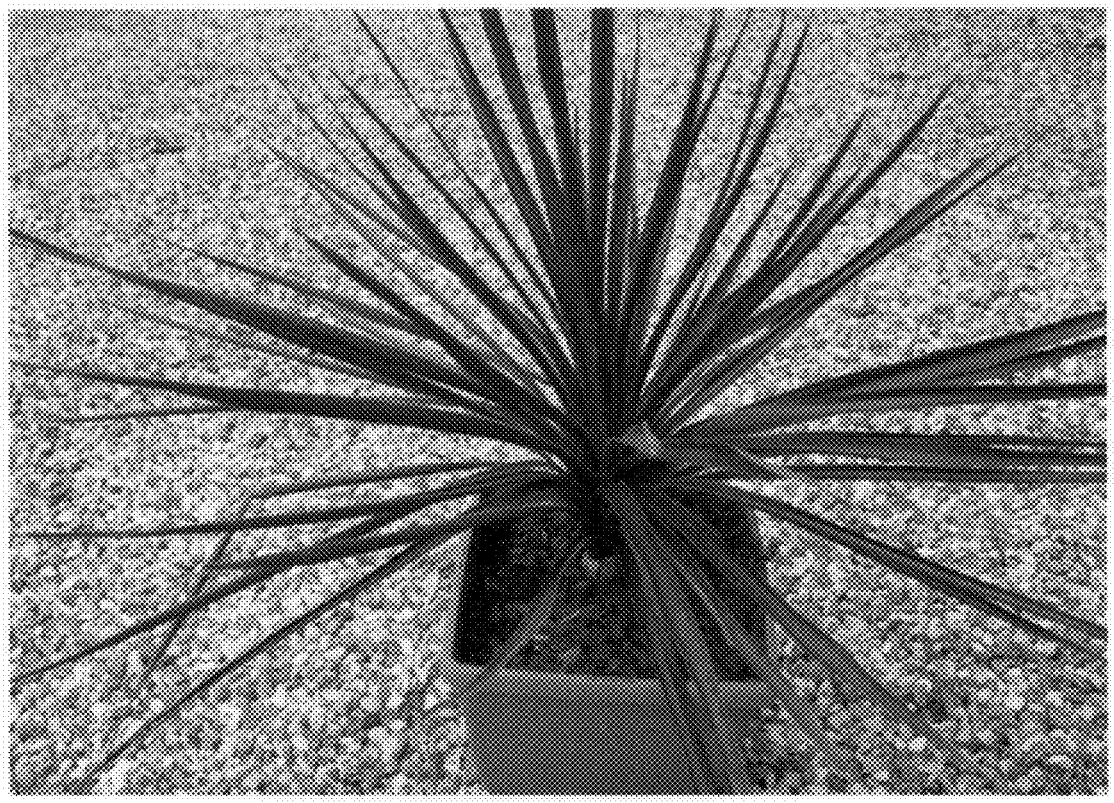
FIG. 2 provides a side view of 'NORFIRE'.
Figure 3:
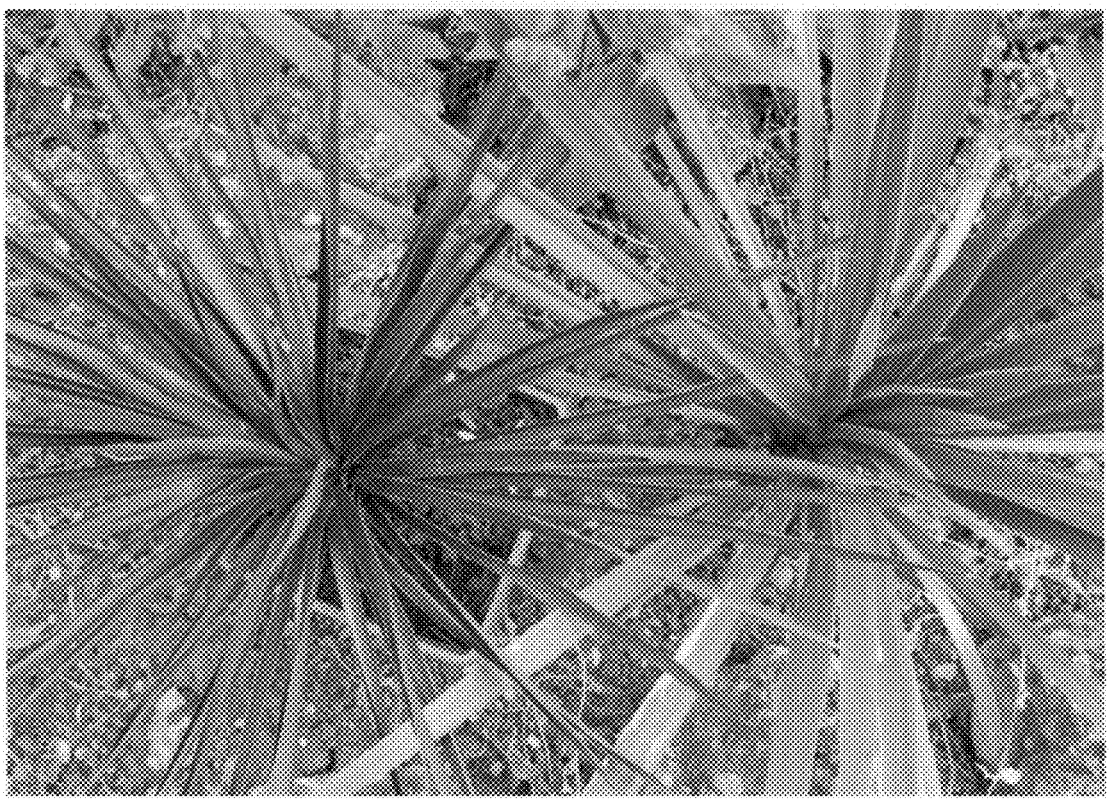
FIG. 3 provides a comparison of 'NORFIRE' on the left and a 3 year-old plant of 'Red Star' on the right (planted from a 25-cm container). The colors in the photographs may differ slightly from the color values cited in the detailed botanical description, which accurately describe the colors of the new *Cordyline.*

The following is a detailed description of 3 year-old plants of the new cultivar as grown under poly cover in a 25-cm container in Preston, Lancashire, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—No flower production has been observed for 'NORFIRE'.

*Plant habit.*—Evergreen tropical perennial, dense, upright and rounded, solitary stem.

*Height and spread.*—Reaches about 39 cm in height and 70 cm in width (3 year-old plant).

*Hardiness.*—U.S.D.A. Zones 9 to 10.

*Culture.*—Well drained soils in full sun in the United Kingdom.

*Diseases and pests.*—No unique susceptibility or resistance to diseases or pests has been observed.

*Root description.*—Fibrous.

*Propagation.*—Tissue culture.

*Growth rate.*—Moderate, vigor typical to other cultivars of *Cordyline australis*.

Stem description:

*Stem length.*—6 cm to lowest leaves on 3 year-old plants.

*Stem width.*—Average of 2 cm on 3 year-old plants.

*Stem cross-section.*—Round, solid.

*Stem surface.*—Cork-like.

*Stem color.*—Primarily N187A.

Foliage description:

*Leaf shape.*—Linear.

*Leaf division.*—Simple.

*Leaf base.*—Narrowing into an indistinctly defined sheathed petiole.

*Leaf apex.*—Acuminate.

*Leaf venation.*—Longitudinal, parallel, not distinct, in high light lateral parallel veins are 181D in color with mid-rib 186C in color.

*Leaf margins.*—Entire, not undulate.

*Leaf attachment.*—Clasping.

*Leaf arrangement.*—Densely, spirally arranged in terminal rosette.

*Leaf number.*—An average of 50 leaves (about 30% more leaves than parent plant).

*Leaf orientation.*—Held upright with older leaves at various angles to form a rounded overall plant shape.

*Leaf substance.*—Thick, leathery.

*Leaf surface.*—Glabrous and glossy on upper surface, glabrous and dull on lower surface.

*Leaf aspect.*—Concave and very weakly keeled on lower surface with the keel becoming more prominent where the leaf and petiole join.

*Leaf color.*—Young and mature leaves upper and lower surface; closest to N187A (slightly more brown) with a marginal band (<0.5 mm in width) 185C, under garden conditions when light passes through the foliage, the color is nearer 181A with narrow veins and margins 181D and mid-rib 186C.

*Leaf size.*—Average of 33 cm in length and 13.5 mm at mid point on 3 year-old plants.

*Petiole.*—Weakly defined about 4 cm in length with expanded portion 2 cm in length at clasping base and 1 cm in width, color of upper surface is 163D heavily streaked with 183A and 157A near attachment, color of lower surface is N187A with very narrow margin (<0.5 mm in width) 185C in color, surface of upper surface is glabrous and glossy and surface of lower surface is glabrous and dull.

*Flowering.*—No flower production has been observed to date for 'NORFIRE'.

It is claimed:

1. A new and distinct cultivar of *Cordyline* plant named 'NORFIRE' as herein illustrated and described.

* * * * *